United States Patent

Bonnet et al.

[11] Patent Number: 6,052,616
[45] Date of Patent: Apr. 18, 2000

[54] METHODS AND APPARATUS FOR PROVIDING A CRITERION OF EXTRA-SYSTOLE FREQUENCY AND GRAVITY

[75] Inventors: Jean-Luc Bonnet, Montrouge; Anne Bouhour, Ville d'Avray, both of France

[73] Assignee: Ela Medical S.A., Montrouge, France

[21] Appl. No.: 09/093,812

[22] Filed: Jun. 9, 1998

[30] Foreign Application Priority Data

Jun. 9, 1997 [FR] France .................................. 97 07115

[51] Int. Cl.⁷ ................................................ A61B 5/0472
[52] U.S. Cl. ................................................ 600/515; 607/9
[58] Field of Search ...................... 600/515, 519, 600/518, 521; 607/14, 9, 4, 5

[56] References Cited

U.S. PATENT DOCUMENTS

| | | | |
|---|---|---|---|
| 5,312,451 | 5/1994 | Limousin et al. | 607/15 |
| 5,423,863 | 6/1995 | Felblinger et al. | 607/5 |
| 5,513,645 | 5/1996 | Jacobson et al. | 607/27 |
| 5,645,576 | 7/1997 | Limousin et al. | 607/19 |

FOREIGN PATENT DOCUMENTS

| | | | |
|---|---|---|---|
| 0 550 342 | 7/1993 | European Pat. Off. | A61N 1/368 |
| 2 717 397 | 9/1995 | France | A61N 1/365 |

*Primary Examiner*—Kennedy J. Schaetzle
*Attorney, Agent, or Firm*—Orrick, Herrington & Sutcliffe LLP

[57] ABSTRACT

An apparatus and process for the determination of criterion of a frequent presence or of the gravity of atrial and/or ventricular extra-systoles in an active implantable medical apparatus. The signals corresponding to cardiac events in at least one cardiac cavity are detected and the occurrence of extra-systoles are detected. At the detection of every extra-systole, a ponderation (i.e., weight or magnitude of increment) is attributed to the extra-systole, and a count of extra-systoles with the attributed ponderation applied for the detected extra-systole is made. The count also is decremented at each detected cardiac cycle not having a detected extra-systole, such that the decrement also may have an associated ponderation. The count thus provides a criterion of extra-systole frequency and gravity (seriousness).

19 Claims, 4 Drawing Sheets

METHODS AND APPARATUS FOR PROVIDING A CRITERION OF EXTRA-SYSTOLE FREQUENCY AND GRAVITY

FIELD OF THE INVENTION

The present invention concerns an active implantable medical device, more particularly a device of the family of pacemakers, defibrillators and cardiovertors, which is able to deliver electrical pulses to the heart in response to a determination of a criterion of the frequent occurrence or seriousness (gravity) of extra-systolic events (atrial or ventricular), as well as to a process for determining a criterion of a frequent occurrence or gravity of an extra-systole, for the control of such a device. Such active implantable medical devices are defined, for example, in the directive 90/385/EEC of Jun. 20, 1990 of the European Community Council.

BACKGROUND OF THE INVENTION

There are implantable active medical devices, such as the well known double chamber devices, which collect (sense or detect) and deliver (stimulate) signals in the high (atrial) and low (ventricular) cavities of the heart. These apparatus are conceived in order to follow the cardiac rhythm of a patient and to perform one or more functions for the diagnosis and/or therapy of atrial (AA) and/or ventricular (AV) arrhythmias. These diagnostic and therapeutic functions, which are also known as control functions, are executed in response to the arrhythmias (AA or AV) that present a predefined pattern, with isolated extra-systoles, extra-systoles occurring in salvos, and the so-called troubles of rhythm (abnormally fast rhythms), but they could be operating improperly based on changes between these different patterns due to extra-systolic events. The consequence can be an inappropriate diagnosis, with a possibly of the application of a therapy that is inappropriate and perhaps harmful.

Generally, one defines two types of ventricular extra-systoles (ESV). A ventricular extra-systole of the first type corresponds to a detection or ventricular stimulation which is not preceded by an atrial event (i.e., a detection of a spontaneous beat or a stimulation pulse delivered by the device in the atrium) in a time interval considered as physiological, for example, between 31 and 300 ms. A ventricular extra-systole of the second type corresponds to a ventricular detection preceded by an atrial event in an interval of time between 31 and 300 ms, in the case where the atrio-ventricular delay (AR) of the examined cycle is more than 31 ms less than the atrio-ventricular delay period (DAV) of the preceding cardiac cycle (DAV–AR>31 ms), a cardiac cycle being defined as the interval of time between two events of a similar nature in the same cavity. For further details on the processing of ventricular extra-systoles, reference is made EP A 550 342, and its corresponding U.S. Pat. No. 5,312,451 which is incorporated herein by reference, describing an algorithm of specific actions after the detection of a ventricular extra-systole.

A "P" wave or an "event P' (the collection of a spontaneous cardiac event having its origin in the atrium) is defined as an atrial extra-systole (ESA) if the interval of time separating this P wave from the preceding atrial event is less than a fraction of the average interval of the atrial frequency calculated over a number cardiac cycles, e.g., eight cycles, not comprising an extra systole (average PP).

Further, one finds defined in the literature a class of extra-systoles known as doublets (double) or triplets (triple), that are, respectively, a continuation of two extra-systoles (ESA or ESV) without an intermediary event not of extra-systolic origin or a continuation of three extra-systoles without an intermediary event not of extra-systolic origin. These extra-systole doublets or triplets occur according to a sequence of some repetition.

There also is known the so-called "salvo" of extra-systoles, which is a sequence of very close repetitions of extra-systoles (atrial or ventricular) presenting multiple events without any intermediary event not of an extra-systolic origin. These extra-systole salvos are cardiac events that are worrisome, and their presence is a sign of the seriousness or gravity of the cardiac prognosis of the patient. Salvos of extra-systoles can necessitate the delivery of a defibrillation shock, if they degenerate in the ventricle into a fibrillation.

One defines also a trouble of the sustained rhythm as salvoes whose duration is greater than a predetermined time (typically 30 s).

OBJECTS AND SUMMARY OF THE INVENTION

An object of the present invention is to provide a process and a device able to determine a criterion of the frequent occurrence or gravity of extra-systolic events (atrial or ventricular), that is, isolated extra-systoles and salvos of extra-systoles, with a view either to stop a control function that is under way, or to inhibit the release of another type of control function, or on the contrary, to authorise the release of a specific control function.

To this end, an active implantable medical device according to the present invention comprises a means for detecting a cardiac activity signal in at least one cardiac cavity, means for detecting an occurrence of extra-systoles, a extra-systole counter, means for incrementing the extra-systole counter at the detection of each extra-systole, and means for decrementing the extra-systole counter at each cardiac cycle in the absence of a detected extra-systole.

In order to determine a criterion of frequent occurrence or gravity of extra systole, one observes, according to a process of the invention, the value of the extra-systole counter of the active implantable medical device over the course of consecutive cardiac cycles. When the counter count reaches a predetermined threshold, the appropriate control function can be stopped or released as appropriate.

One aspect of the invention, advantageously, is directed to a process which comprises the following. One detects cardiac activity signals in at least one cardiac cavity. One detects the occurrence of extra-systoles in the cardiac activity. One increments a counter at the detection of each extra-systole. One decrements the counter at each cardiac cycle in which an extra-systole is not detected.

Very advantageously, it is foreseen to provide a means (or, in the process, a step) for attributing a first ponderation (namely, a weighted increment as will be explained) at each detection of an extra-systole. In this case, the incrementing of the extra-systole counter is advantageously realized with application at the detection of each extra-systole of the ponderation that is associated with it. Thus, the ponderation thus may progressively or otherwise increase the amount added to the counter with each successive extra-systole. Similarly, the decrementing of the counter at each cardiac cycle not having a detected extra-systole is advantageously realised with the application of a second associated ponderation.

In addition, in one preferred embodiment of the invention, the extra-systole counter may have at least one predetermined counting threshold, such that the device (and similarly the process) according to the invention also includes means (or a step) of inhibiting and/or releasing specific control functions of the active implantable medical device (e.g., for awakening a specific control function, activation and deactivation) if a pre-determined threshold of the extra-systole counter is crossed.

Further, in an advantageous manner, one can determine the position of each extra-systole in a salvo by an appropriate monitoring means for processing the acquired signals. Preferably, in such case, the ponderation has a proper value for each extra-systole according to the position of the extra-systole in the salvo and its frequency of appearance.

An extra-systole is considered to be frequent if it is separated from the last detected extra-systole by a minimum number of cycles (typically 8) without an intervening extra-systole.

The described device of the present invention also allows one to establish a criterion of frequent occurrence of extra-systoles. In this case, an extra-systole is considered frequent if the number of successive extra-systoles is greater than or equal to 1 (that is, at least two successive extra-systoles less than 8 cycles apart). It is said to be not frequent in the opposite case (two successive extrasystoles more than 8 cycles apart).

In another advantageous embodiment of the invention, the ponderation is realised by employing an arithmetical or geometrical progression with a predetermined modulation. The modulation can depend on the particular arrhythmia found to exist for each control function to be inhibited or released. Preferably, the ponderation(s) are integer multiples.

Preferably, too, the extra-systole counter is set or reset to zero by an initialization means. In another preferred embodiment, the initialisation of the extra-systole counter can be caused by an external programming of the active implantable medical device, and in an advantageous manner the extra-systole counter is limited to zero as its lowest value.

BRIEF DESCRIPTION OF THE DRAWINGS

Further characteristics, features and advantages of the invention will appear to the person of ordinary skill in the art, in view of the following detailed description, made with reference to drawings annexed, in which.

DETAILED DESCRIPTION OF THE INVENTION

Figure 1:
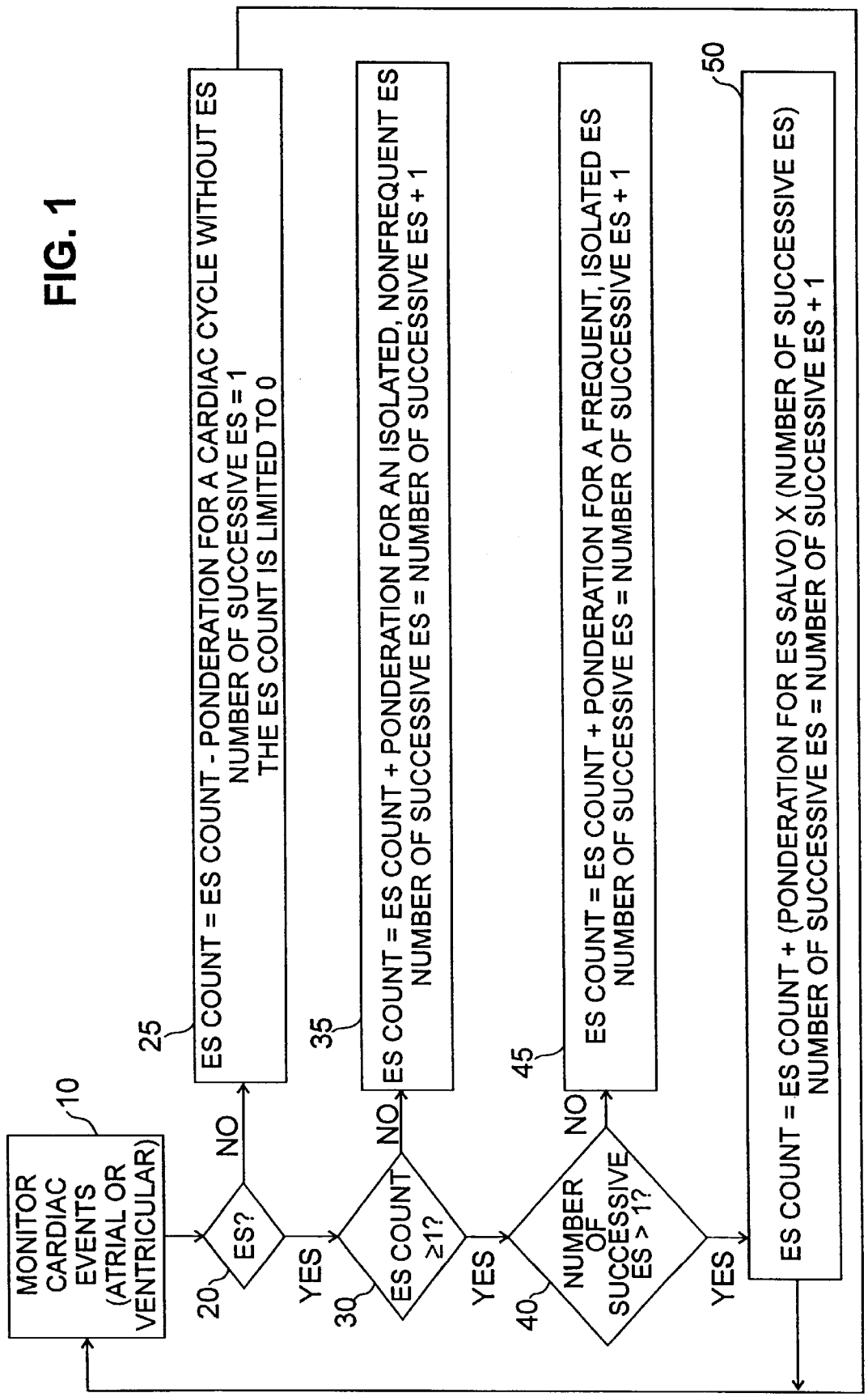
FIG. 1 is a schematic diagram of a preferred embodiment of the extra-systole counter according to the invention.

Referring to FIG. 1, the operating principle of the extra-systole counter according to the present invention is shown. At the initialisation of the system the extra systole counter ES is set to zero. In a manner well known to a person of ordinary skill in the art, one monitors and detects, by the active implantable medical device, events occurring in the atrial chamber A or the ventricular chamber V of the heart (stage 10), and further one detects the appearance of extra-systoles (stage 20). If an isolated extra-systole (ES) is determined (stage 30, no), the extra-systole counter ES is incremented by applying a typical ponderation, for example, a count of 8 if the extra-systole is considered as not frequent (stage 35) and a ponderation of 1 in the opposite case (stage 40, no; stage 45). If the extra-systole is a salvo (stage 40, yes), the extra-systole counter is typically incremented by an arithmetical progression with a determined ponderation, for example, of 1, multiplied by the number of the extra-systoles detected in the salvo (stage 50). In the absence of an extra-systole (stage 20, no), one decrements at each cycle the ES counter with the associated ponderation, typically of 1 (stage 25).

Figure 2:
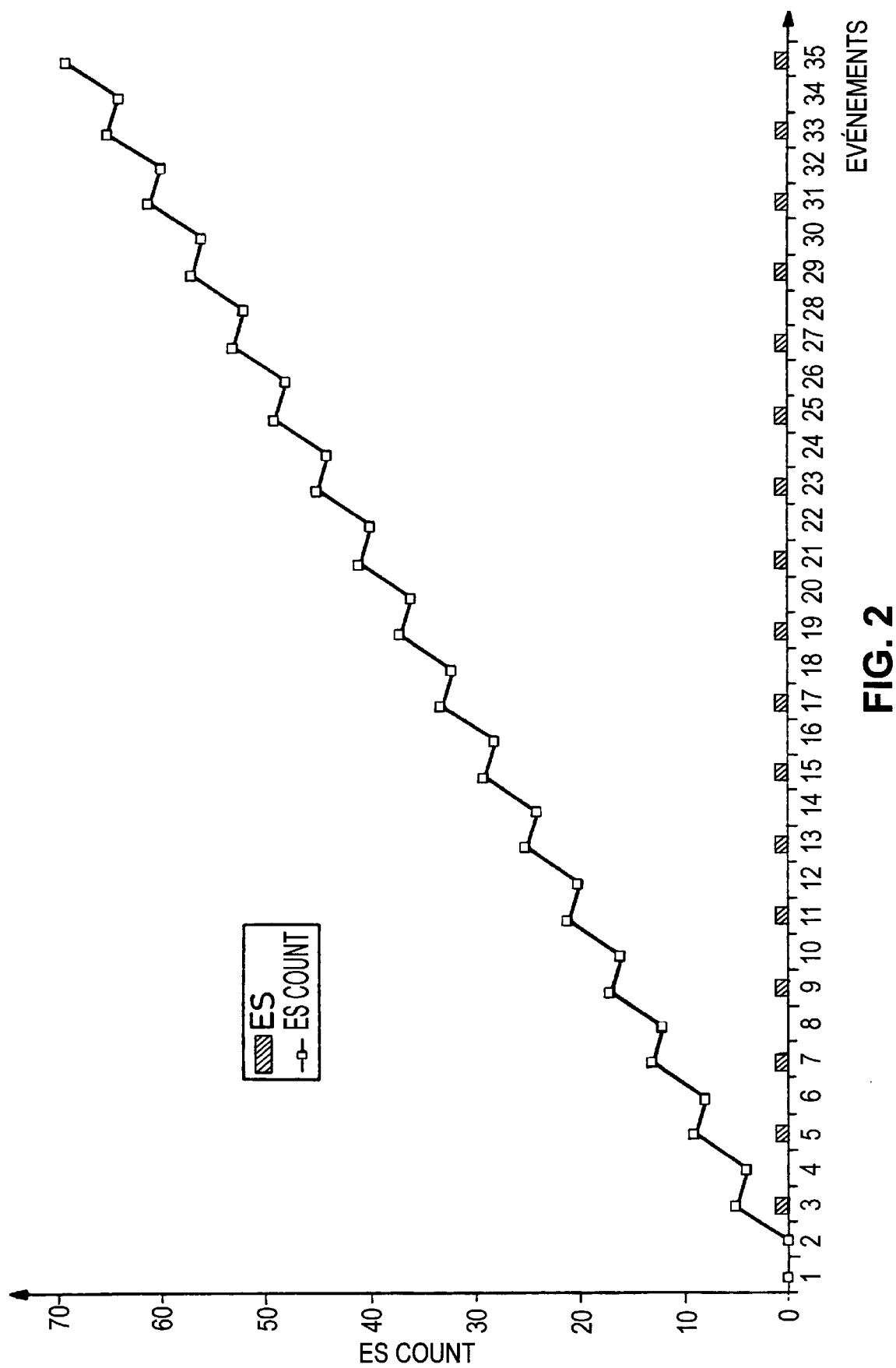
FIG. 2 is a representation of extra-systole counter values as a function of events appearing over the course of different cardiac cycles according to a first example of a preferred embodiment.
Figure 3:
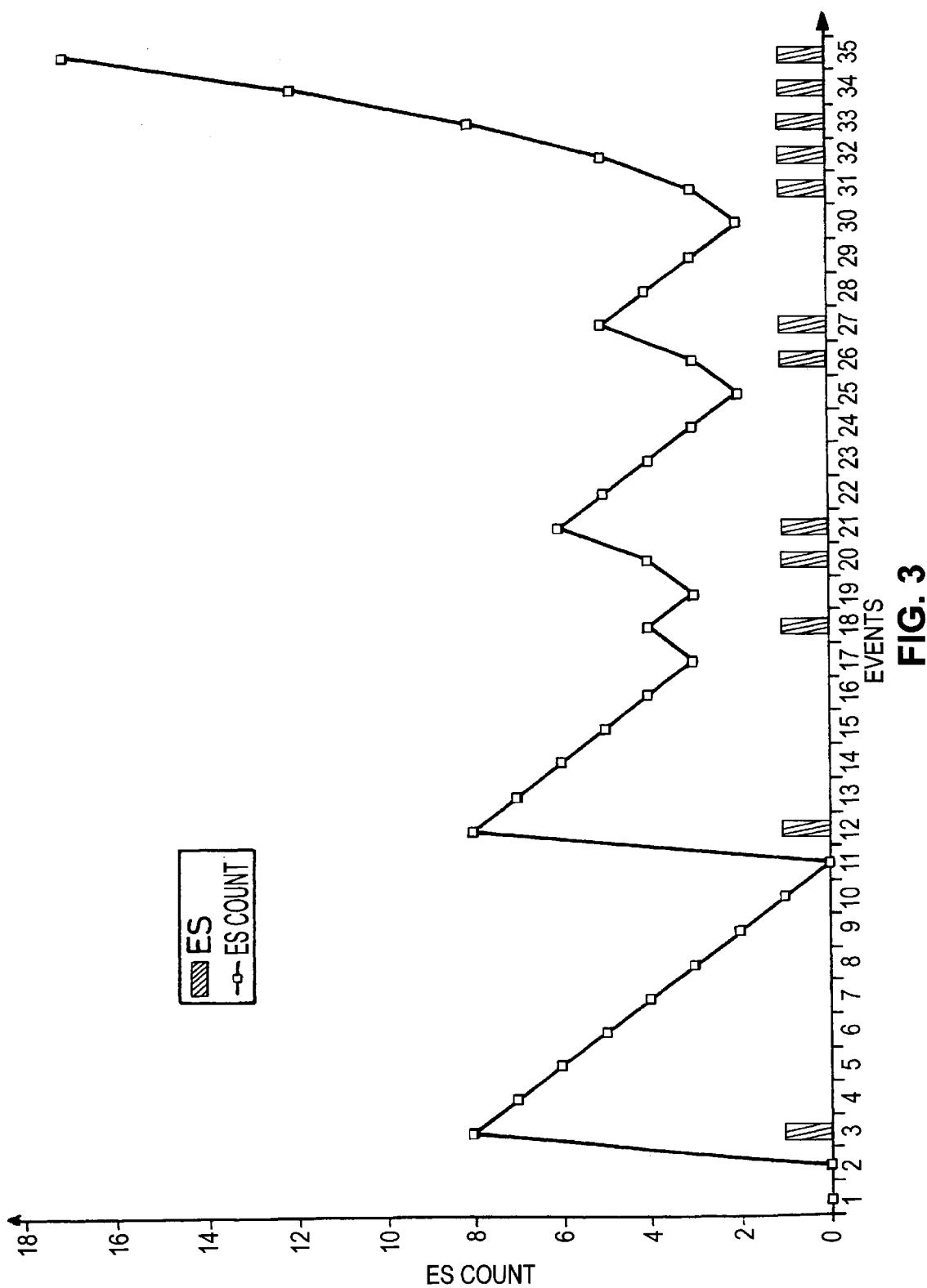
FIG. 3 is a representation of extra-systole counter values as a function of events appearing over the course of different cardiac cycles according to a second example of a preferred embodiment.

In FIGS. 2 and 3, the rate of extra-systole corresponds to the value of the extra-systole counter ES. A second counter counts the number of successive extra-systoles indicating thus the "number" of the extra-systole occurring inside a given salvo.

In the case of a doublet of extra-systoles, the extra-systole counter is therefore incremented by one at the detection of the first event forming the doublet and by two, for example, on the second event. Other ponderations are possible as, for example, five on the first event and ten on the second.

Preferably, ponderations are selected as an integer multiple. However, in a general manner, a ponderation can have any value.

For example, in the case of a salvo of extra-systoles, the counter is incremented by a value that is a multiple of the number of the extra-systole occurring in the salvo. In an preferred example, the ponderation is a multiple of 1. The extra-systole counter ES is therefore incremented 1 on the first event and 2 on the second. For a ponderation corresponding to a multiple of 5, the counter ES will be incremented 5 on the first event, 10 on the second, 15 on the third and so on.

The modulation of the ponderation can follow a geometrical progression at the detection of each extra-systole, or again each extra-systole in a salvo can have a specific attributed ponderation.

On any other cycle (spontaneous or stimulated event without an extra-systole) corresponding to the collection of a P wave (an atrial detection) or an R wave (a ventricular detection) or at a stimulation, the extra-systole counter ES is typically decremented by one unit (stage 25). Preferably, the extra-systole counter ES is limited to zero as its lowest value.

The ponderation that is applied on each detection of an extra-systole on the one hand, and on each cardiac cycle without an extra-systole on the other hand, as well as the modulation, allow to reveal certain disturbances of the cardiac rhythm, designated under the term of "patterns".

If one considers, for example, a "bigeminy" (a repetition of an extra-systole on two cardiac cycles) it will be appropriate to associate a large ponderation (or multiple) with the subject pattern as that shown in FIG. 2, where the ponderation corresponds to a multiple of five.

The invention allows, therefore, to differentiate the gravity or seriousness of some events. In the example of a typical ponderation value of 1 for cycles with extra-systole and without extra-systole, 10 isolated extra-systoles occurring in 60 cardiac cycles are less serious than a salvo of 10 consecutive extra-systole. In the second case, the extra-systole counter will calculate, for example, values 1+2+3+4+5+6+7+8+9+10=55.

In a more general manner, if a particular pattern or repetition is studied with a ponderation particular to each element of the pattern, then it will be revealed easily at the time of the counting. The use of the counting and the ponderation permits identifying the pattern representing the studied arrhythemia easily, e.g. a bigeminy as illustrated in FIG. 2. Similarly, the notion of frequency of appearance of extra-systoles will be able to be revealed by an appropriate choice of the ponderation and the decrementing of the counter.

For example, as illustrated in FIG. 3, one can attribute a ponderation (increment) of 8 to an isolated extra-systole or to the first extra-systole of a salvo if it is not frequent, and a ponderation of 1 if it is a frequent extra-systole. Then, one increments the extra-systole counter of 2, 3, etc. at occurrence of the second, third, etc. extra-systole respectively, within a salvo. On the other hand, at each cardiac cycle without an extra-systole occurring, one decrements the extra-systole counter by 1.

Following the control functions implemented in the device, one will be able to associate with them a value of a predetermined count threshold of the extra-systole counter ES, such that on crossing the threshold an appropriate control function will be activated or de-activated, according to the case. The control function can then be reactivated if the threshold is crossed in the other direction, or if the count reaches another threshold value, different from the preceding threshold (such as to account for the effect of hysteresis).

The control function of placement in awakening (activation) of functions of defibrillation (namely, deliverance of a high energy shock) will be able to be activated for large values of the extra-systole counter ES (e.g., start charging a shock capacitor). If the counter crosses a second value, greater than this first threshold, the function in question will be able then to be released (triggered) (i.e., deliver a defibrillation shock pulse). Consequently, when the extra-systole counter is below this first threshold, the function is not put in functioning, and an economy of current from the energy source can be realised.

Also, for each control function, one can implement one or more thresholds for activating it or de-activating, as the case may be.

For example, in a preferred mode of implementation of the invention, according to the FIG. 3, one releases a control function, for example, the acceleration of the cardiac stimulation rhythm, on the occurrence of an atrial extra-systole if the value of the extra-systole counter is greater than or equal to 1, and one inhibits the control function if the value of the extra-systole counter has crossed the threshold of 16, that is to say the count is above this threshold and so it is stopped. In this last case, the engaged function has failed.

Figure 4:
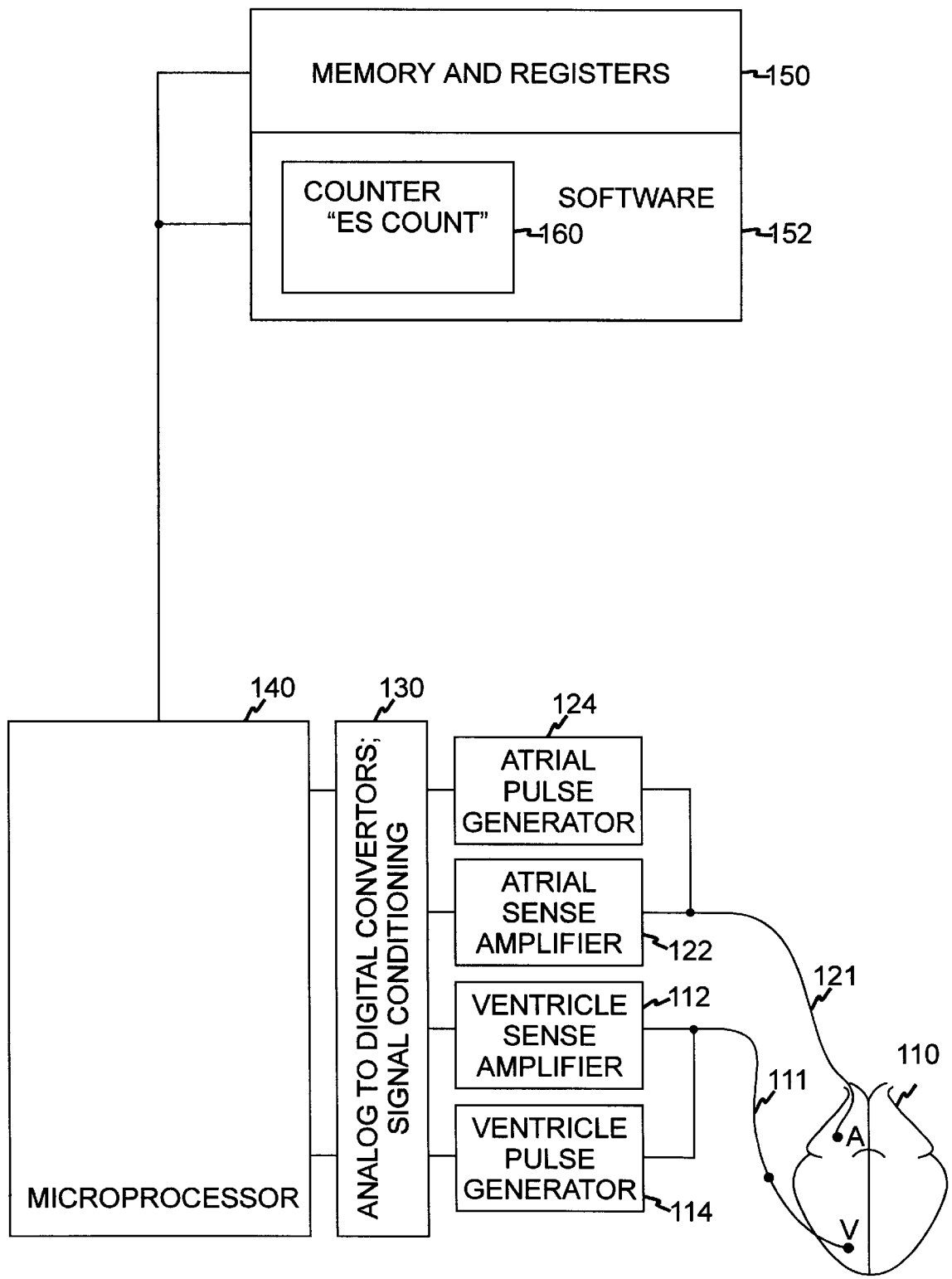
FIG. 4 is a block diagram of the apparatus of a preferred embodiment of the invention.

As illustrated in FIG. 4, the detection of atrial and ventricular complexes and the measuring of the amplitude of these atrial and ventricular complexes are performed by conventional electronic means, e.g., digital microprocessor controlled devices having sense amplifiers, e.g., ventricle sense amplifier 112 and atrial sense amplifier 122 analog to digital conversion circuits 130 and microprocessor 140 with software 152 and suitable memory and registers 150 for data processing and manipulation. These devices also include an atrial pulse generator 124 and a ventricle pulse generator 114 for stimulating the atrium and ventricle under device control. The present invention is preferably implemented under software control, and occurs following acquisition of the cardiac electric signals by a conventional sense amplifier, e.g., by sensing electrical activity in the heart 110 atrium A and ventricle V using cardiac leads 111 and 121, preferably after the acquired signals have been conditioned and converted to digital form in the usual manner. Accordingly, the parameters of the algorithm are programmable. A suitable counter 160 is preferably implemented in and controlled by the software 152 to perform the aforementioned functions so as to maintain and update (increase in response to a detection of ES or decrease in response to an absence of ES) the ES count and to adjust the ES count as illustrated in FIG. 1 and discussed above. Representative electronic circuits of this embodiment are those found in the series of pacemakers available from ELA Medical, Montrouge, France, offered under the CHORUS trademark.

As would be understood by a person of ordinary skill in the art, the foregoing may be implemented in an active implantable medical device by use of discrete circuits (analog and/or digital circuits) or, alternatively, by a microprocessor based device operating under software control. Indeed, software suitable to perform the above described operations is believed to be easily written by and within the abilities of a person of ordinary skill in the art and may be stored in suitable memory, e.g., ROM, or in firmware.

In addition, because the cardiac event sensing and counting need not require any additional circuits (other than the conventional circuits for acquiring cardiac event information and conditioning those signals for processing by a microprocessor with memory typically already existing in the device), software for processing such data in accordance with the present invention may advantageously be loaded into a RAM memory (or programmable non volatile memory) of microprocessor based device. Thus, software may be transferred by conventional telemetry into an already implanted device, and then programmed to operate or not operate as appropriate or as needed. Such conventional medical devices that might use the invention are known and include, for example, the OPUS brand single chamber cardiac pacemakers, the CHORUS brand dual chamber cardiac pacemakers, and the Defender brand defibrillators all of which are available from ELA Medical S.A., Montrouge, France, the assignee hereof.

One skilled in the art will appreciate that the present invention can be practiced by other than the described embodiments, which are presented for purposes of illustration and not of limitation.

We claim:

1. An active implantable medical device comprising:
    a) means for detecting a signal indicating cardiac activity of at least one cardiac cavity and determining a cardiac cycle;
    b) means for detecting an occurrence of an extra-systole in said cardiac cavity;
    c) an extra-systole counter;
    d) means for incrementing the extra-systole counter in response to each detection of an extra-systole, and
    e) means for decrementing the extra-systole counter in response to an absence of a detected extra-systole in a detected cardiac cycle.

2. The device according to claim 1, further comprising means for attributing a ponderation to each detection of an extra-systole.

3. The device according to claim 2, wherein the means for incrementing further comprises means for applying, at the detection of each extra-systole, the attributed ponderation that is associated with the detected extra-systole.

4. The device according to claim 2, further comprising means for detecting a salvo of extra-systoles and means for determining the position of each extra-systole in said salvo.

5. The device according to claim 4 further comprising means for determining a frequency of occurrence of an extra-systole, wherein the ponderation has an attributed value for each extra-systole according to its position in the salvo and the frequency of occurrence of the extra systoles.

6. The device according to the claim 5, wherein the ponderation further comprises one of an arithmetical progression and a geometrical progression type with a predetermined modulation.

7. The device according to claim 2, wherein the ponderation further comprises an integer multiple.

8. The device according to claim 1, wherein the means for decrementing further comprises means for applying a ponderation to the decrement of the extra-systole counter at each cardiac cycle in the absence of a detected extra-systole.

9. The device according to claim 1, wherein the extra-systole counter further comprises at least one threshold of counting, and further comprising means for comparing the counter count to the counting threshold and means for inhibiting and releasing operation of a control function of the active implantable medical device in response to said at least one counting threshold being crossed.

10. The device according to claim 1, further comprising means for initialising the extra-systole counter to zero.

11. The device according to claim 10, further comprising means for initiating the initialisation of the extra-systole counter in response to an external programming of the implantable active medical device.

12. The device according to claim 1, wherein the extra-systole counter is limited to a lowest value of zero.

13. A process for the determination of a criterion of a frequent presence or gravity of extra-systole for the control of an active implantable medical device, comprising:

a) detecting cardiac activity signals in at least one cardiac cavity;

b) detecting a cardiac cycle;

c) detecting an occurrence of an extra-systole in said cardiac signals;

d) incrementing a count of extra-systoles at the detection of each extra-systole;

e) decrementing the count of extra-systoles in the absence of a detected extra-systole in a detected cardiac cycle; and f) providing a criterion of the extra-systolic frequency or gravity as a function of said count.

14. The process according to claim 13, further comprising attributing a ponderation to each detection of an extra-systole.

15. The process according to claim 14, wherein incrementing the count of extra-systoles at the detection of each extra-systole further comprises applying the attributed ponderation in said increment.

16. The process according to claim 14, further comprising:

g) identifying a salvo of extra-systoles; and h) determining a position of each extra-systole in said identified salvo.

17. The process according to claim 13, further comprising associating a ponderation with a detected absence of an extra-systole in a detected cardiac cycle, wherein the step of decrementing at each cardiac cycle the count of extra-systoles in the absence of a detected extra-systole in a detected cardiac cycle further comprises applying said associated ponderation to said decrement.

18. The process according to claim 13 further comprising:

g) providing a threshold of counting;

h) comparing the count of extra-systoles to the threshold of counting; and i) responding to the count of extra-systoles crossing the threshold of counting to control an operation of a control function.

19. The process according to claim 18 wherein step i) further comprises one of releasing a control function and inhibiting a control function.

* * * * *